United States Patent [19]

McCroskey et al.

[11] Patent Number: 5,138,642
[45] Date of Patent: * Aug. 11, 1992

[54] DETECTOR IMAGING ARRANGEMENT FOR AN INDUSTRIAL CT DEVICE

[75] Inventors: William K. McCroskey, Solon; David S. Vickers, Macedonia; Roland W. Carlson, Cleveland; Robert L. Zahn, Bainbridge; Jack A. Drobny, Seven Hills, all of Ohio

[73] Assignee: Innovative Imaging Systems, Inc., Cleveland, Ohio

[ * ] Notice: The portion of the term of this patent subsequent to Jun. 11, 2008 has been disclaimed.

[21] Appl. No.: 471,856

[22] Filed: Jan. 29, 1990

Related U.S. Application Data

[63] Continuation-in-part of Ser. No. 317,767, Mar. 2, 1989.

[51] Int. Cl.[5] .................................................. A61B 6/00
[52] U.S. Cl. .................................. 378/19; 378/22; 378/62
[58] Field of Search ............... 378/19, 99, 22, 57, 378/62; 250/213 VT, 62, 98, 99, 361 R, 363.01, 363.82, 368; 350/254; 358/111

[56] References Cited

U.S. PATENT DOCUMENTS

| | | | |
|---|---|---|---|
| 3,758,723 | 9/1973 | Green et al. | 178/6.8 |
| 4,255,666 | 3/1981 | Wang et al. | 250/486 |
| 4,298,800 | 11/1981 | Goldman | 250/445 T |
| 4,426,721 | 1/1984 | Wang | 378/99 |
| 4,506,327 | 3/1985 | Tam | 364/414 |
| 4,604,649 | 8/1986 | Carollo et al. | 358/111 |
| 4,675,739 | 6/1987 | Catchpole et al. | 358/213.11 |
| 4,736,397 | 4/1988 | Velasquer | 378/99 |
| 4,829,552 | 5/1989 | Rossi et al. | 378/99 |
| 4,931,647 | 6/1990 | Hiruma et al. | 250/368 |
| 4,987,307 | 1/1991 | Rizzo et al. | 250/368 |
| 5,023,895 | 6/1991 | McCroskey et al. | 378/4 |

Primary Examiner—Janice A. Howell
Assistant Examiner—Don Wong
Attorney, Agent, or Firm—Renner, Otto, Boiselle & Sklar

[57] ABSTRACT

A detector arrangement is disclosed for an industrial CT x-ray system which uses a three dimensional cone beam to irradiate the specimen and a large two dimensional scintillation screen to develop a light image corresponding to the energy of the attenuated radiation beams. The light image is focused by a special lens arrangement with zoom capability onto the photocathode of an intensifier. The intensified light image developed is transmitted by fiberoptics to a plurality of CCD chips, each chip developing electrical signals corresponding to a segment of the image developed in the intensifier. The chips are clocked in a predetermined manner based on a prior information developed in an initial scan to produce a high resolution image of large industrial objects in a short time.

17 Claims, 7 Drawing Sheets

CCD TIMING
INTENSIFIER ON/OFF
SYSTEM GATING

DETECTOR IMAGING ARRANGEMENT FOR AN INDUSTRIAL CT DEVICE

This is a continuation-in-part of prior co-pending application Ser. No. 317,767 filed Mar. 2, 1989, which is incorporated in its entirety by reference herein and made a part and parcel hereof (hereinafter "prior invention").

This invention relates generally to computerized tomographic systems and more particularly to the imaging arrangement used in such systems.

The invention has been specifically developed for and is particularly applicable to hard radiation, industrial x-ray imaging and inspection applications and will be described with particular reference thereto. However, it will be appreciated to those skilled in the art that the system disclosed herein could have broader application and could be used in the medical field or in other applications which desired the direct production of large images of an irradiated object.

INCORPORATION BY REFERENCE

The following documents are incorporated by reference herein and made a part and parcel hereof:
1) the prior invention, Ser. No. 317,767 filed Mar. 2, 1989;
2) Wang U.S. Pat. Nos. 4,255,666 and 4,426,721;
3) Green U.S. Pat. No. 3,758,723;
4) Catchpole U.S. Pat. No. 4,506,327; and
6) Goldman U.S. Pat. No. 4,298,800.

The U.S. patents cited above are incorporated herein by reference as background material so that the description of the invention as set forth herein need not explain conventional structure and operating principles.

BACKGROUND

A) Prior Invention

In the prior invention (application Ser. No. 317,767), an industrial computerized tomographic system is disclosed which has as one of its principal features, when compared to other systems, a very fast scan time. One aspect of the prior invention which is significant with respect to the fast scan time, is the use of a three dimensional cone shaped beam of hard radiation to irradiate the scanned object. A truncated attenuated beam of radiation then impinges upon a two dimensional detector arrangement to produce data which is digitized and used in the computer to reconstruct images of the object. The present invention relates to an arrangement or a system which converts the energy in the attenuated radiation beams into digitized data which is then subsequently used to reconstruct three dimensional object images, etc. (hereinafter referred to as "imagers" or "imaging devices").

B) Prior Applications

Image intensifiers applied to x-ray systems are well known. Typical devices are shown in Wang U.S. Pat. Nos. 4,255,666 and 4,426,721. The Wang devices include a sealed housing constructed so as to draw a vacuum which have a metal input window through which attenuated beams of radiation pass. The attenuated x-ray beams, after passing through the metal window, strike a scintillator/photocathode screen and are converted into photoelectrons and, through the electrical potential developed within the intensifier, accelerated, so as to strike an output phosphor display screen. The display screen produces an intensified light image corresponding to the irradiated object. Typically, the image produced in the output plate is viewed by means of a TV camera such as shown in Haendle U.S. Pat. No. 4,658,410 or focused by mirrors into a video process such as shown in Beekmans U.S. Pat. No. 4,809,309. Besides the use of television cameras, such as vidicons and plumbicons, Wang '721 shows that the light from the output window of the intensifier can be directed to photodiodes which function as detectors producing an analog signal which in turn is digitized, etc. Also, Green U.S. Pat. No. 3,758,723 uses an orthicon camera tube in place of the output display screen and the electrons from the photocathode (i.e. light intensifier) are focused by an electromagnetic lens to produce an electron image on a target which is recorded by the orthicon camera tube. All of the arrangements discussed (with the exception of Wang '721) appear to be directed to arrangements which produce two dimension radiographs.

It is known to use charge-coupled devices (hereinafter CCD) in place of the video tubes noted above. For example, Catchpole U.S. Pat. No. 4,675,739 discusses the benefits of CCD devices but notes that such devices are not suited for large area arrays of image sensors. To a similar effect is Goldman U.S. Pat. No. 4,298,800 which discloses a CT application for a fan shaped beam of attenuated radiation which is converted to visible light by a tilted fluorescent screen or a scintillation crystal. The light passes through a lens arrangement which focuses the imaged object directly onto a CCD device. When several CCD devices are used, several different lens systems are employed. While the arrangement disclosed may be acceptable for small fan shaped areas in the medical imaging environment, the multiple lens system employed in Goldman is impractical for industrial application and it is doubtful that signal strength will be sufficient to permit imaging in an industrial environment.

A focusing lens system is also utilized in Green '723 where attenuated x-ray beams pass through a fluorescent screen and are reflected by a mirror orientated at approximately 45° through a lens system which directs the image onto a convex lens photocathode to develop two dimensional radiographs. In Green, the workpiece is intermittently rotated so that the orthigon camera can integrate the image produced while the workpiece is stationary and the time for developing the image is unacceptably slow for systems to which this invention relates. Green is limited to two dimensional radiographs with a field of view of about six inches in maximum dimension at a processing time of about 1 second per view and with a resolution of objects within the view of about 1/30" in measurement. Thus, in Green the size of the field of view, the time for developing the image and the sharpness or picture resolution of the developed image is unacceptable for industrial applications under discussion.

SUMMARY OF THE INVENTION

Accordingly, it is a principal object of the subject invention to provide an industrial, hard radiation imaging and inspection system which can take large views of an irradiated object with sharp resolution in short time periods.

This object along with other features of the invention is achieved in an industrial, non-destructive, inspection and imaging system which includes a source of radiation emitting a cone shaped beam of high radiation at one side of the imaged specimen and a two dimensional scintillation screen at the opposite side of the specimen which receives irradiated beams of the radiation and generates light photons correlated to the intensity of the attenuated radiation beams. A mirror reflects the light emitted from the scintillation screen along an angular axis relative to the screen. A lens arrangement positioned on the angular axis includes a large diameter lens at one axial end thereof which focuses the light photons reflected by the mirror and at the opposite end of the lens arrangement a lens is closely adjacent a flat glass window input plate. The flat glass window plate forms the window at one end of a vacuum sealed and cooled intensifier housing. The intensifier's photocathode is at the plate's interior surface and the lens mechanism is effective to optically focus the visible light reflected by the mirror onto the photocathode. The f number of the lens must be as low as possible so that as much light from the screen can be transferred to the image intensifier photocathode. A flat intensifier screen which is parallel to and spaced a slight axial distance from the photocathode is provided with a conventional electrical arrangement between the photocathode and the screen to generate an electrical potential therebetween whereby the photoelectrons developed at the photocathode are accelerated toward the intensifier screen which produces an intensified pattern of light photons corresponding to the electron pattern. A fiberoptic plate on the opposite side of the intensifier screen and parallel therewith conveys the image to a plurality of generally straight fiberoptic conduits with each conduit having a plurality of fiberoptic bundles arranged in an orderly manner to transmit images from one axial end to the other axial end thereof. The conduits at one axial end are arranged in a side-by-side contact with the fiberoptic plate and substantially encompass the area of the fiberoptic plate while the fiberoptic conduit is laterally displaced from one another at the opposite axial end thereof. A fiberoptic tapered conduit is provided for each straight conduit positioned at the laterally displaced axial end thereof for reducing the size of the image transmitted through each straight conduit, the image transmitted in each conduit reflecting a portion or segment of the field-of-view image contained in the fiberoptic plate. An area CCD device is connected to each tapered conduit for generating in a bucket brigade manner, electrical analog signals corresponding to the two dimensional image shown at the reduced end of each tapered conduit in the CCD devices.

To increase the intensity of the image a multi-channel plate is provided adjacent to the photocathode for multiplying the number of electrons generated by the photocathode. In addition, the intensifier's scintillation screen is a phosphorus screen having a thin vaporized coating of aluminum on its side facing the photocathode for reflecting light photons back toward the fiberoptic plate. Preferably, the intensifier housing is cooled to a temperature of at least $-20°$ C. and preferably $-40°$ C. so that not only the dynamic range of the CCD chips is enhanced while the noise is reduced, but also resolution of the image produced at the phosphorus screen is enhanced. In accordance with the size aspect of the invention, the scintillation screen has a two dimensional size of no less than about $36'' \times 14\frac{1}{2}''$ and the straight fiberoptic conduits adjacent the fiberoptic plate are positioned relative to one another so that a space of no more than about 1-2 pixels exists. Thus, substantially all of the light image produced in the scintillation screen is reproduced with sharp resolution as segmented field-of-view portions produced at the reduced end of each fiberoptic tapered conduit.

In accordance with another aspect of the invention, a magnifying lens flip out arrangement is provided which is movable over and away from the first lens to permit close-up views of a portion of the image produced from the scintillation screen. Importantly, the focal plane of the lens arrangement, with or without the magnifying lens, remains at the photocathode side of the flat glass window so that refocusing of the lens arrangement is not required when the zoom feature of the invention is employed. Additionally, the magnified image has a sharper resolution than the image produced without the zoom lens arrangement in place.

In accordance with another aspect of the invention, the CCD chips, while conventional, are chosen to produce square pixels of a size correlated to the cladding or bundle size of the fiberoptics employed in the arrangement to insure excellent isotropic resolution. The CCD readout mechanism includes shift registers and an amplifier for generating an analog output signal from each CCD chip indicative of the light intensity imaged onto each CCD chip at specific charge or pixel locations. A multiplexer arrangement variably controls the time that the intensifier is cycled off and on, the time during which the CCD readout mechanism is activated, and the gating of the signals. More particularly, an analog to digital arrangement is provided which includes means to amplify the analog signal generated by the CCD readout mechanism, means to modify the amplified analog signal as a logarithmic function to account for the attenuation of the beams of hard radiation and means to offset the logarithmic analog signal to filter noise therefrom, and finally, an analog to digital device is provided to convert the corrected analog signal to a string of digital signals. By processing the analog signals, the time for processing the digitized signals to pixel data is reduced over that which would otherwise be required.

In accordance with a still further feature of the invention, the CCD devices are tapped or read directly without the need for any memory devices because the multiplexer cycles the intensifier on for a fixed time period while the specimen is stationary and during which time the CCD device is charged or integrated. The multiplexer also controls the CCD timing and signal gating so that when the intensifier is cycled off, the specimen is rotated and the CCD device is read without memory storage. Significantly, a priori data is gathered and analyzed by the host computer which analyzes the attenuated radiation data developed in the CCD devices during an initial scan of the irradiated object to control directional movement of the intensifier relative to the mirror to achieve proper focusing of the intensifier, to control positioning of the specimen relative to the source of radiation and to establish the integration time during which the intensifier is cycled on and off by the multiplexer to optimize the scanning time for the imaged object. In this manner, the integrating time for the CCD devices is correlated to the mass density of the imaged specimen to establish an optimum processing speed and the CCD devices are accordingly clocked in a timed relationship to the on/off cycling of the intensifier.

The following are objects of the hard radiation, nondestructive, inspection-imaging system of the invention which exist independently of one another and/or in any combination thereof:

1) Imaging of large objects;
2) Fast imaging time;
3) Sharp image resolution;
4) Low noise;
5) Zoom capability;
6) Optimal processing time of different specimens in one machine; and
7) Low cost.

Still further advantages, objected and features of the invention will become apparent to those of ordinary skill in the art upon a reading and understanding of the following description of the preferred embodiment.

BRIEF DESCRIPTION OF THE DRAWINGS

The invention may take form in certain parts and arrangement of parts, a preferred embodiment of which will be described in detail herein and illustrated in the accompanying drawings which form a part hereof and wherein.

DETAILED DESCRIPTION

Figure 9:
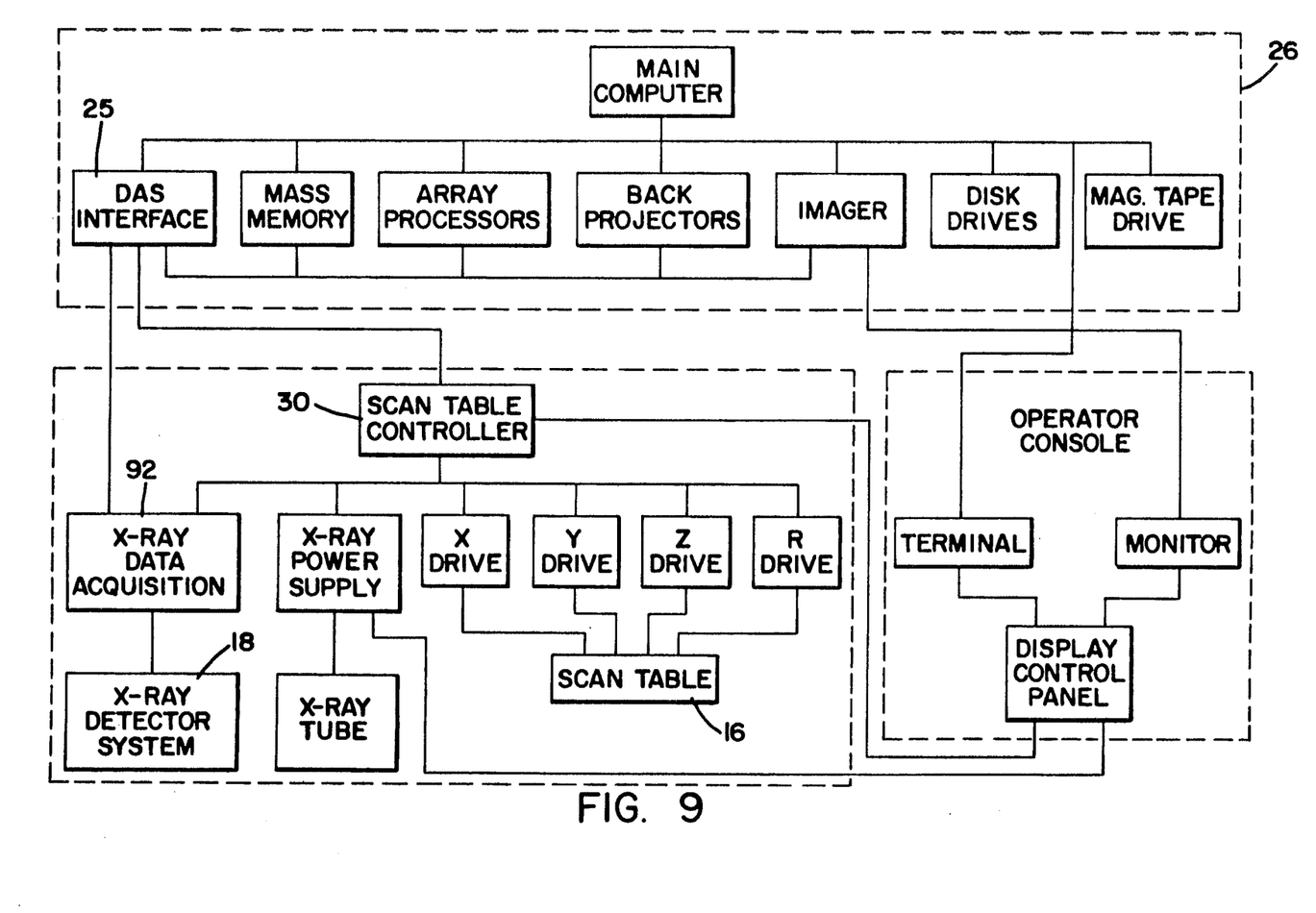
FIG. 9 is a schematic illustration of the scan functions of a CT system employing the present invention and corresponds to FIG. 6 of the prior invention.
Figure 10A:
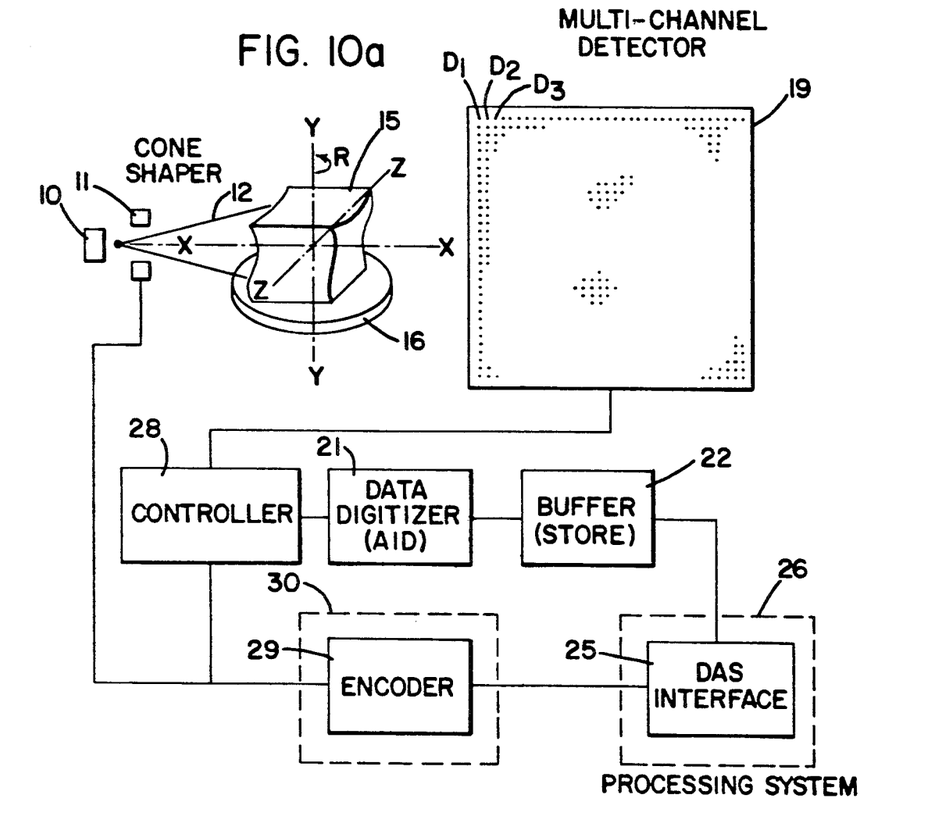
FIGS. 10a, 10b and 10c correspond respectively to FIGS. 12a, 12b and 12c of the prior invention and schematically illustrate a portion of the x-ray data collection system disclosed in the prior invention.
Figure 10B:
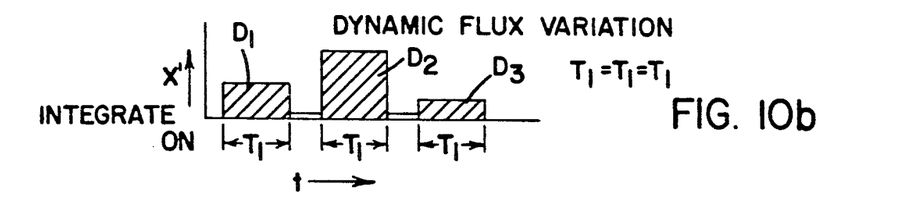
Figure 10C:
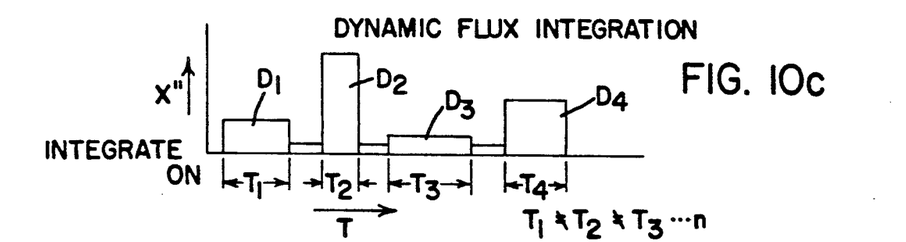

Referring now to the drawings wherein the showings are for the purpose of illustrating a preferred embodiment of the invention only and not for the purpose of limiting the same, reference should be first had to FIGS. 9 and 10 and to a description of the CT system which is disclosed and discussed in the specification of the prior invention which is incorporated herein by reference and made a part and parcel hereof. Reference is thus first had to FIGS. 9 and 10a where a source of hard radiation 10 develops, vis-a-vis a cone shaper 11, a three dimensional cone shaped beam of hard radiation 12 which irradiates a specimen 15 placed on a scan table 16. The energy of the attenuated radiation beams is collected in an x-ray detector system 18. In the prior invention, detector system 18 included a multi-channel detector 19 which basically comprised a plurality of detectors D1, D2, D3, etc. arranged in a two dimensional array such that each detector was indicative of a pixel. The detectors D are of the current integrating type and are serially digitized in an analog to digital data digitizer 21 and stored in buffer 22 which acts as a high speed memory. The digitized data is then transferred through the data acquisition system interface 25 into the main computer processing system shown as dotted line 26 in FIG. 9 where the image is then reconstructed. As discussed in the prior invention, a controller 28 which is a part of the scan table controller 30 controls an encoder 29 to control the intensity and shape of cone shaped beam 12 while also controlling the readings of detectors D from multi-channel detector 19. U.S. Pat. No. 4,506,327 to Tam which was incorporated by reference in the parent patent application and is likewise incorporated by reference in this application, discloses the use of a priori information from an initial scan to vary the flux or the intensity of the x-ray beam as shown in FIG. 10b. Alternatively, the time of integration of detectors D as shown in FIG. 10c can be varied to account for significant changes in the attenuated radiation beams. In the present invention, the a priori information contained in an initial scan effected by rotating scan table 16 through at least a portion of a rotation is used to collect data in the processing system 26 which determines, for constant or variable energy of x-ray source 10, the time, which in the preferred embodiment is constant, at which detectors D are on so as to develop a sufficient time for an appropriate integration signal to develop. Also, the main processing unit controls the scan table controller 30 to establish the optimum position of scan table 16, the speed of rotation of the table when the detectors D are off, the degree of rotation, etc. Thus, in the preferred embodiment of the invention, the integration time for detectors D is constant although, in alternative embodiments, the time or the flux can be varied as graphically demonstrated in FIGS. 10b and 10c or the time and the flux can both be varied. In the alternative embodiments, insofar as this invention is concerned, either the time of integration or the flux intensity is varied for the particular two dimensional image which is being recorded. That is, as specimen 15 rotates to a new position where its density has increased, the integrating time may be increased or decreased for all detectors or the flux increased or decreased for all detectors to compensate for the change in mass density. In such applications, detectors $D_1$, $D_2$, $D_3$, etc. shown in FIGS. 10b and 10c would be replaced by scan or angle positions so that $D_1$ would be the position of specimen 16 at table angle $R_1$, $D_2$ would be table angle $R_2$, etc.

Figure 1:
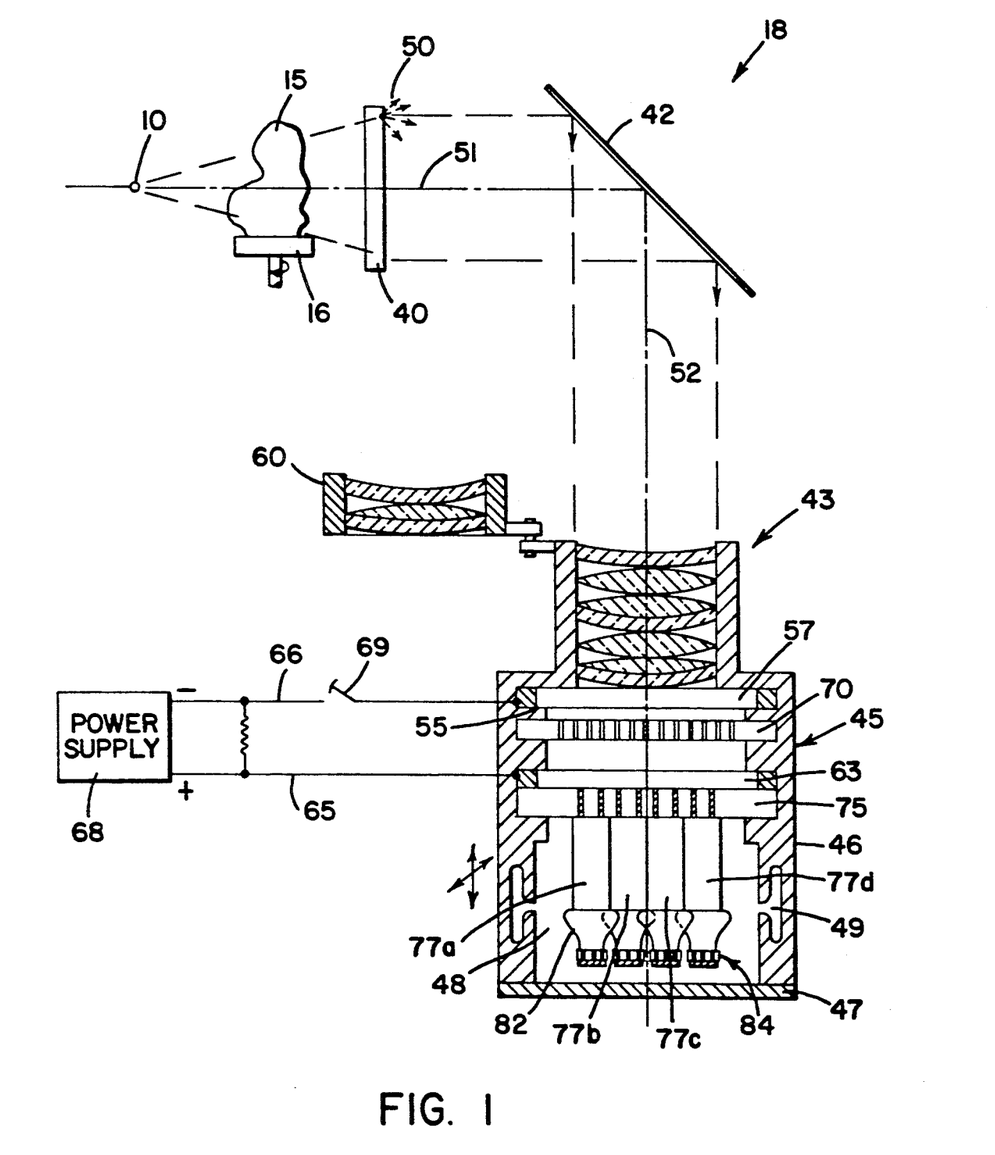
FIG. 1 is a schematic sectional view of the imaging detector arrangement of the present invention.

Referring now to FIG. 1, detector system 18 is shown to comprise as major components, a scintillation screen 40, a mirror 42, a lens arrangement 43, and an intensifier 45. The entire arrangement is encased within a shielded enclosure (not shown), the window of which is defined by scintillation screen 40. Thus, scan table 16, with its appropriate encoders and x, y and z drives controlled thereby, positions specimen 15 relative to radiation source 10 to optimize the attenuated beams of radiation impacting scintillation screen 40 in a manner as defined in the prior invention. Reference may be had to application Ser. No. 317,767 for a detailed description of the positioning arrangement. As will be appreciated by those skilled in the art, the intensity of the attenuated beams of radiation in an industrial CT system is significantly less than what otherwise occurs with respect to medical CT systems and the like. When a cone shaped three dimensional radiation beam is utilized, the problem becomes severe especially when contrasted with fan shaped and pencil beam systems of the prior art. Thus, to the extent that provisions must be made in a cone shaped CT system of the type disclosed herein to obtain an attenuated beam intensity sufficient to generate an adequate visible light image from scintillation screen 40, the prior invention forms a part and parcel of the present invention. Also to the extent that digitized data is used in a CT system to reconstruct an image of the specimen as disclosed in the prior patent is required in the present invention, the prior invention forms a part of this invention.

Scintillation screen 40 is of a minimum dimensional size of 14½"×36". Screens of such size are commercially unavailable. Preferably, screen 40 is constructed of conventional scintillation crystals such as cesium iodide doped with thalium. Since the size at which such crystals can be grown is limited, screen 40 is made up of several such screens placed in line-to-line contact with one another, i.e. a mosaic. More particularly, screen 40 would have 3 crystals of approximately 12"×14½" surface dimension which would be placed side by side to form a "mosaic" screen. Such a crystal mosaic, scintillation screen will generate lines at the interface between adjacent crystals and this in turn will require an averaging between adjacent pixels where the line would occur in the image to remove the lines from the reconstructed image. Obviously, some degradation in picture quality will occur. Alternatively, a fluoroscopic screen such as one utilizing gadolinium oxysulfide or zinc cadmium sulfide could be employed although the scintillation crystal is preferred. In accordance with known principles, an attenuated x-ray beam strikes scintillation screen 40 and emits light photons 50 which radiate in all directions and which are correlated in energy (wavelength, color) to the energy of the attenuated x-ray beam.

A large, plane glass mirror 42 reflects the light emitted from scintillation screen 40 to the lens arrangement 43. Mirror 42 is at least equal in size to scintillation screen 40 and is offset at an angle, preferably 45°, to a central axis 51 of x-ray source 10 and also to an angular axis 52 which is the central axis of lens arrangement 43 and intensifier 45. Thus, the angular or lens axis 52 forms a right angle with x-ray axis 51. Mirror 42 is used to minimize any incident radiation from source 10 impacting intensifier 45 and thus increases its useful life. Mirror 42 is flat.

Figure 2:
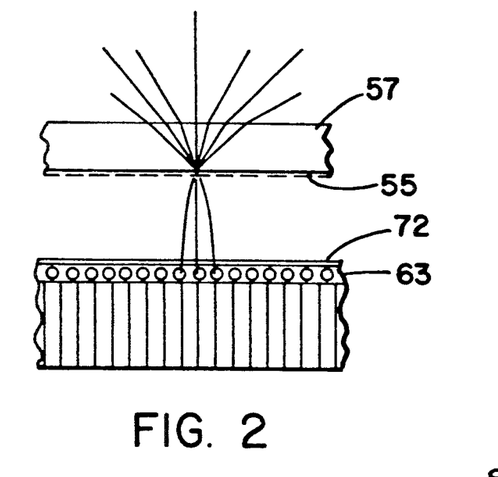
FIGS. 2, 3, 4, 5 and 6 are schematic, fragmentary views of various components of the intensifier schematically illustrated in FIG. 1.

Substantially all of the image reflected by mirror 42 is focused by lens arrangement 43 onto photocathode 55 of intensifier 45. For drawing purposes, lens arrangement 43 is shown as part of light intensifier 45. In practice, lens arrangement 43 is fixed relative to intensifier 45 but it need not be a part of intensifier 45. (The sizing and stacking of the lens, per se, is conventional and existing copyrighted computer programs can be used to size the various lenses in the package to insure consistent focusing of all visible light colors. In the preferred embodiment, the lens arrangement utilized is supplied from D.O. Industries. A lens diameter of approximately 7" has been found sufficient to focus substantially all of the image reflected by mirror 42 onto photocathode 55 of intensifier 45. Unlike conventional proximity intensifiers which have either a metallic window or a lens window, intensifier 45 has a heavy, flat glass plate window 57 (which provides a simple and inexpensive means to vacuum seal one axial end of intensifier 45) with photocathode 55 at its interior surface. The lens arrangement 43, as shown in FIG. 2, is designed to focus the light at the inside surface of input glass window 57 so that any problem with flare does not occur. A two dimensional drive arrangement (not shown) which permits movement in the direction of the arrows shown in FIG. 1, is also provided for intensifier 45 and lens arrangement 43. This drive arrangement provides for movement along intensifier axis 52 to permit focusing at photocathode 55. Thus, the arrangement disclosed controls image resolution not only by the positioning of scan table 16 through scan table controller 30 but also by the intensifier drive which is activated by controller 28 or, alternatively, by scan table controller 30. Additionally, a flip out magnifying lens arrangement 60 is provided. Importantly, zoom lens arrangement 60 is designed so as not to change the focal point of lens arrangement 43 so that the drive does not have to be actuated for close-up views which can be imaged instantaneously. Placing the zoom lens 60 in front of lens arrangement 43 also provides a resolution increasing feature, i.e. sharper image without having to refocus lens arrangement 43. To provide for an appropriate scanning by the imaging arrangement with the magnifying lens 60 in place, the drive arrangement for intensifier 45 can also move in a direction perpendicular to angular axis 52, i.e. in or out of the plane of the drawing. For the lens arrangement 43 discussed, zoom lens 60 increases the magnification by a factor of 13 to 1. Further increases are possible by providing additional flip-in lenses (not shown) which can simply serially stack one on top of the other. It is to be appreciated that while the sizing and positioning of various lenses to achieve focusing at a point is conventional, the incorporation of lens arrangement 43 into the detector arrangement with its unique zoom, drive and photocathode-flat glass plate focus comprise unique and important features of the present invention.

Referring now to FIGS. 1 and 2, as previously indicated, photocathode 55 is provided at the interior surface of flat glass plate input window 57. A flat phosphorus screen 63 parallel to and spaced axially a slight distance away from photocathode 55 is grounded to intensifier 45 and a photocathode electrode 66 with an electrode attached to phosphorus screen 63 is connected to a power supply 68 to develop a high voltage electrostatic potential therebetween in a conventional manner. Reference may be had to the intensifier patents discussed above for a more detailed explanation than that provided herein. Photocathode 55, phosphorus screen 63, power supply 68, electrode 65, 66 are conventional. A switching mechanism shown schematically at 6: nd under the control of controller 28 or scan table controller 30 is provided for turning intensifier 45 off and on at predetermined intervals as will be discussed in greater detail hereafter. As shown in FIG. 2, intensifier 45 as thus far described operates in a conventional manner in that photoelectrons at photocathode 55 are accelerated and strike phosphor screen 63 with increased intensity to produce light photons which leave screen 63.

To further increase the intensity of the photoelectrons striking phosphorus screen 63, a multi-channel plate 70 is provided in the space between photocathode 55 and phosphorus screen 63 to increase the number of photoelectrons striking phosphorus screen 63. The multi-channel plate is conventional and can be purchased from any number of conventional sources such as ITT.

The intensified light image leaving phosphorus screen 63 is conveyed exclusively by fiberoptics to the CCD chips. To prevent flareback of the light photons towards multi-channel plate 70 a thin coating of aluminum or other suitable metal is applied, preferably by vacuum deposition technique, to the side of phosphorus screen 63 facing photocathode 55. On the opposite side of phosphorus screen 63 is a fiberoptic plate 75. This plate is the same size as the phosphorus screen 63, multichannel plate intensifier 70 and photocathode 57. For the arrangement under discussion all items are parallel to one another and approximately 7" in diameter. Ideally, if a CCD chip could be constructed of this size, the chip would simply be mounted flush onto the backside of fiberoptic plate 75. Because there is a limit to the size of CCD devices which are presently produced and commercially available, the image reflected through fiberoptic plate 75 is reduced in size to accommodate presently available CCD devices by a fiberoptic arrangement which is able to capture substantially all the image reflected by fiberoptic plate 75 without serious distortion thereof.

Figure 3:
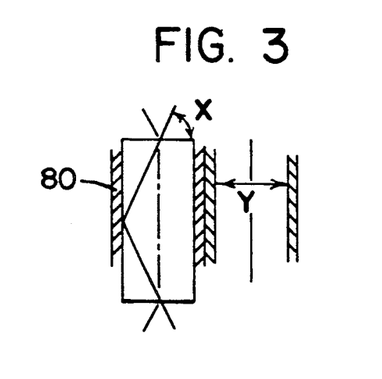
Figure 4:
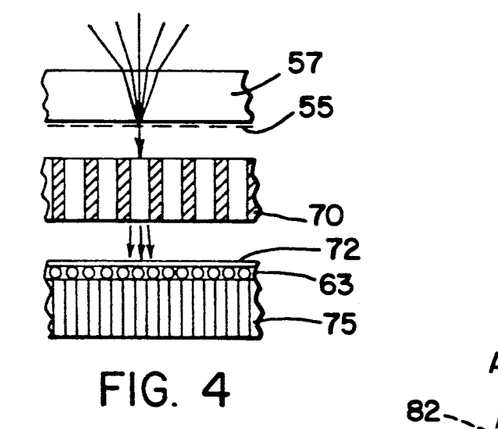
Figure 5:
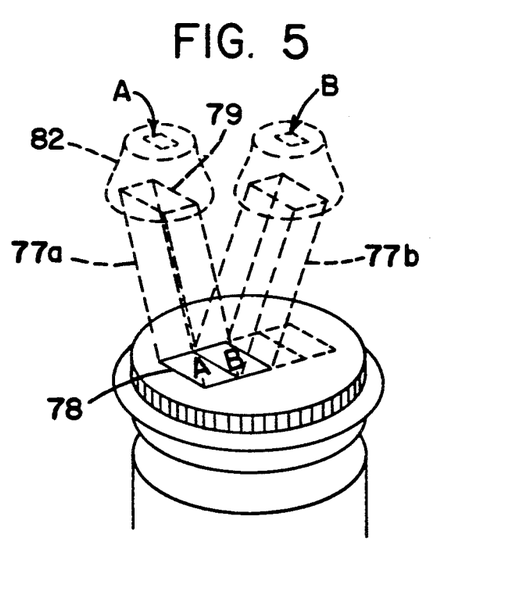
Figure 6:
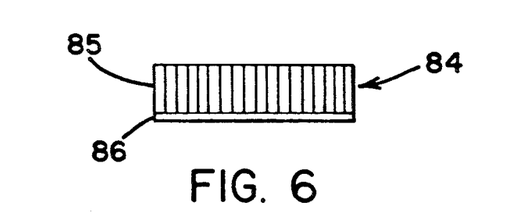

As best shown in FIGS. 1 and 5, this is accomplished by arranging the fiberoptics in a plurality of straight conduits 77, there being four such conduits 77a, 77b, 77c and 77d for the arrangement shown. The conduits are rectangular in cross-section and have flat axial bottom and top axial end surfaces 78, 79 which are parallel to fiberoptic plate 75 although the side surfaces of conduit 78 are at an angle relative to the face of fiberoptic plate 75. In fact, conduits 77 are parallelpipeds and each adjacent parallelpiped, i.e. 77a-77b, 77b-77c, 77c-77d, is canted in the opposite direction so that the bottom end surfaces 78 are adjacent one another while the top axial end surfaces 79 are spaced apart from one another in the shape of a "V" as best shown in FIG. 5. The angle, "X", which conduit 77 makes with the face of fiberoptic plate 75 as best shown in FIG. 3 is established at a value which would not hinder or distort transmission of light through the glass fibers encased within cladding 80 or fiber bundles which make up conduits 77. The cladding or optic bundle dimensions is set or established at a "Y" distance or dimension of approximately 6 microns. Axial ends 78 of conduit 77 in contact with fiberoptic plate 75 can be positioned adjacent one another so that a distance of no more than about 1-2 pixels (as defined hereafter) exists. Thus, the image produced through fiberoptic plate 75 is divided, for the arrangement shown, into four portions, two adjacent ones being designated A and B in FIG. 5 and are reflected through the light conduits with minimum distortion. A line does exist between adjacent conduits 77. This is not significant and, as discussed above, can be averaged out by the host computer in reconstructing the image of the object with known, conventional algorithms.

Since each image portion reflected at output end 79 of each conduit 77 is much larger than the dimensional size of conventional CCD chips, a fiberoptic reducer 82 is used to reduce the size of each image portion A, B, etc. to a size which can be projected onto a CCD chip. In accordance with known technique, tapered reducer 82 is sized to have a larger base than output end 79 so that the center bundles of the glass fibers in reducer 82 convey the image portion which is viewed. The image reducers 82 and conduits 77 can be procured commercially from fiberoptic manufacturers such as InCom, Inc.

Referring now to FIGS. 1, 6, 7 and 8, at the end of each fiberoptic reducer is a CCD device 84. The device chosen for the arrangement disclosed is available from Thomson-CSF, a division of Silicium, as Model TH-7883 and this particular CCD device has a fiberoptic plate 85 to which the ceramic CCD chip 86 is attached. The Thompson chip 86 has electrodes 87 arranged in the form of a rectangular grid connected in a conventional manner to conventional shift registers 88. The CCD device functions in a conventional manner and will not be explained in detail herein. Suffice it to note that silicon devices will generate electrons from incident photons which correspond to the entire visible range of light from blue to near infrared. The photogenerated electrons can be collected in a regularly spaced array of photosites 90, each photosite containing a charge packet of electrons with the charge directly proportional to the incident radiation at that photosite and representing the intensity of the image focused at the photosite. Because each of the charge packets corresponds to pictures elements, or pixels, then the number of photosites or pixels determines the resolution of the final image. The charge packets are then transferred in parallel into a CCD shift register 88 where they are transferred serially to an output port. The output of CCD device would then be a series or string of electrical analog signals whose amplitudes represents the intensity of the image at each pixel.

Figure 7:
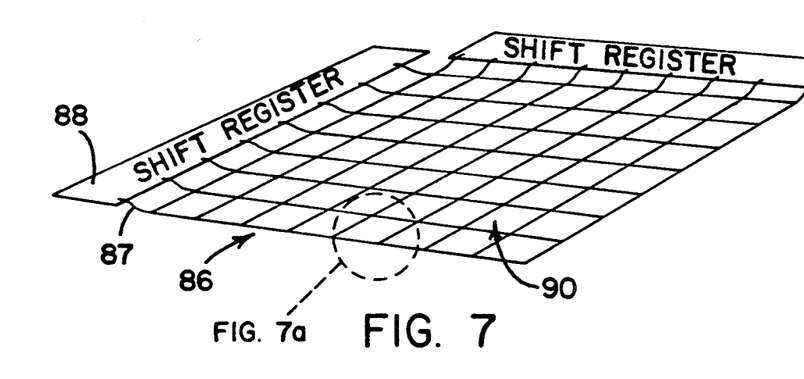
FIG. 7 is a schematic illustration of the electrode grid formed from the CCD chip shown in FIG. 6.
Figure 7A:
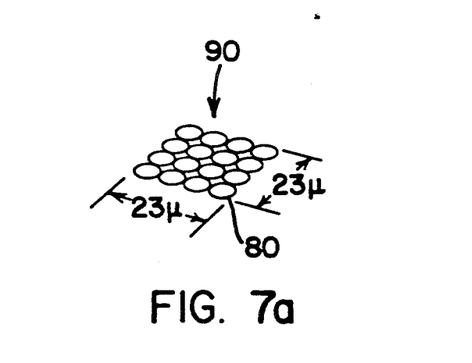
FIG. 7a shows, for relative scaling purposes, the spacing of the fiberoptic cladding within one pixel of the electrode grid shown in FIG. 7.

Importantly, the CCD device 84 is chosen to have a square grid or pixel which gives good isotropic picture resolution. Also, pixel 90 has a dimension of about 23 microns which allows about 24 fiberoptic bundles 80 to be focused thereon to give excellent pixel resolution. Again, each CCD device is clocked or timed to read the charge produced in the rows at one shift register and the charge produced in the column at the other shift register in the manner of a bucket brigade, and the analog signals produced at the shift registers are subsequently digitized and correlated to their precise pixel location.

It is to be appreciated that intensifier 45 is only schematically illustrated in FIG. 1. However, intensifier 45 has preferably a lined or shielded housing 46 with appropriate arrangements made to seal flat glass input window 57 to housing 46 and a bottom plate 47 to the opposite axial end of housing 46 to define a sealed enclosure 48 which contains all the elements of the intensifier. A vacuum is drawn in enclosure 48 in accordance with conventional intensifier practice and an opening 49 in communication with chamber 48 is provided for cooling the intensifier such as with liquid nitrogen. It is, of course, known that CCD devices are noise sensitive and that when cooled, the noise is appreciably reduced and the bandwidth sampling range increased. More specifically, it is known that for every 7° C. drop in temperature, the noise from the CCD device is halved. Intensifier 45 is operated at a minimum temperature of −20° C. and preferably at a temperature as low as −40° C. Because chamber 48 houses not only CCD devices but also the photocathode arrangement, it was found that the photocathode arrangement performed more efficiently at lower temperatures. The intensity of the electrons striking phosphor screen 63 is increased such that a sharper image is outputted from screen 63.

Figure 8:
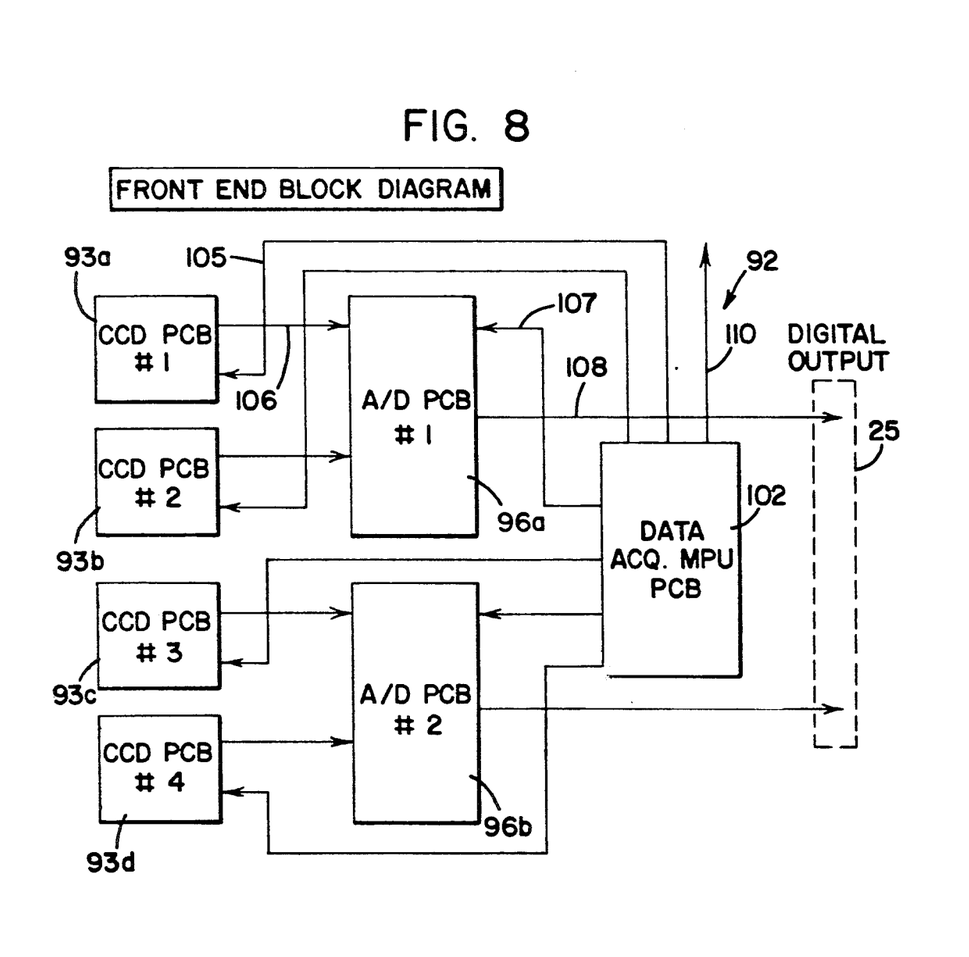
FIG. 8 is a schematic block diagram of the detector circuitry.
Figure 8A:
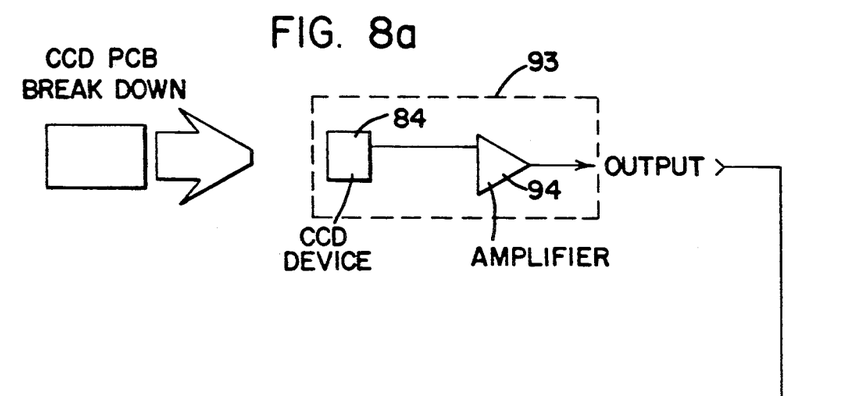
FIGS. 8a, 8b and 8c are block diagrams of various components shown in FIG. 8.
Figure 8B:
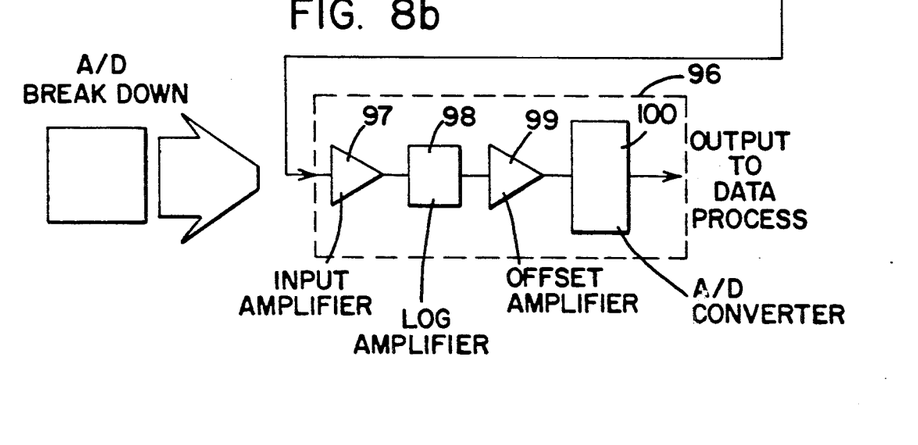
Figure 8C:
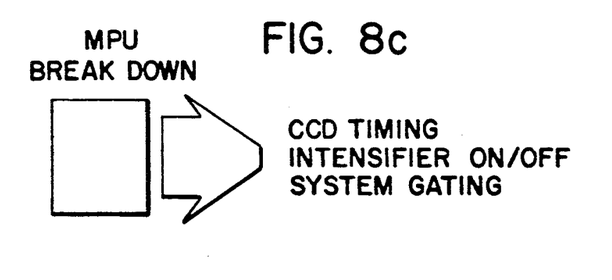

Referring now to FIGS. 8, 8a, 8b and 8c and 9, there is shown in block schematic form in FIG. 8 the x-ray data acquistion system 92. Data acquisition system 92 includes a printed circuit board for each charge-coupled device shown as 93a, 93b, 93c and 93d, an analog-digital printed circuit board 96a, 96b and a data acquisition multiplexer printed circuit board 102. The function of each board will be explained. The circuits which make up each board are conventional, can be readily established by one skilled in the art from the functional description and will not be illustrated or described in detail herein. The CCD output as shown in FIG. 8a is conventional and includes an amplifier 94 at the output gate of each CCD device 84. Reference may be had to Catchpole U.S. Pat. No. 4,675,739 for a description of circuitry used to read out an X-Y CCD array. It is noted that there is no memory storage or buffer used in conjunction with tapping the output of the CCD device in CCD board 93. As best shown in FIG. 8b, the output from CCD board 93 is transmitted to analog to digital board 96 which includes an input amplifier 97 to further amplify the signal and a log amplifier 98 which modifies the signal based on the log function. The log analog signal resulting from log amplifier 98 is then added, substracted, averaged in an adder or offset amplifier 93 before the signal is converted into a digital signal by analog to digital converter 100. Taking the log of the analog signal prior to digitizing the signal has been done in the medical imaging art and significantly reduces the time it would take to correct for the intensity of the attenuated radiation beams if the correction had to be made by the computer from the digitized data. The digital signal as described in the prior invention is transferred to high speed memory device or buffer and the data acquisition system interface 25 where it is then processed by the main computer to reconstruct the image. Referring now to FIGS. 8c and 8, multiplexer 102 contains the timing circuits needed to clock the output from the CCD board 93 vis-a-vis line 105. Also, multiplexer 102 has timing circuits to control gating of the output from CCD boards 93 to A/D board 96 and from A/D board 96 to DAS interface 25 via lines 106, 107 and 108 to insure that the digital data string sent to DAS interface 25 is sent from CCD board 93a first and then from CCD board 93b while simultaneously data from CCD board 93c is sent before data from CCD board 93d through A/D. Additionally, multiplexer 102 controls the on/off cycle time of intensifier 45 via line 110.

As discussed above, specimen 15 is initially rotated through a scan or partial scan at which time scan table controller adjusts the and X, Y, Z and R drives of scan table 16 to optimize the image developed on scintillation screen 40 as explained in detail in the prior invention. Also, the intensifier drive is actuated to focally position the lens arrangement 43. Importantly, from the a priori information developed in the scan, processing system 26 determines the appropriate time that the CCD devices 84 are to be exposed to the light image to develop sufficient electrons in the charge packets to permit image reconstruction. That timing information is then used through controller 28 which is a subpart of scan table controller 30 to establish the on time of intensifier 45, i.e. the time the CCD devices integrate, and the off time during which the R drive is actuated to rotate specimen 15 to its next predetermined angle. That is, the object is rotated through a predetermined angle and stopped and the intensifier turned on for a predetermined time during which the CCD devices 84 are charged. Intensifier 45 is turned off and rotated to its next angle and during the off time the CCD devices 84 are read out through the block diagram shown in FIG. 8. The readout time is, of course, very short so that the off time is actually a function of the speed of the rotating drive and total system cycle time. Typically, the on time for metal objects imaged by the device is generally in the range of 100 milliseconds and the "off" time during which rotation occurs is about 60-70 milliseconds. Thus, the start and stop of the CCD timing cycles are fixed or controlled in a variable manner by the time at which the intensifier is variably controlled in its on/-off cycles. As discussed above, in the preferred embodiment of this invention, the intensifier on/off cycles are fixed for the entire scan but the cycles could be varied as diagrammatically indicated in FIG. 10c or, alternatively, the radiation source may be varied as shown in FIG. 10b. Of course, it is recognized that when the system is used to inspect and image a number of identical parts, an appropriate fixture is used so that only one initial scan need be established for the entire run.

The invention has been described with respect to the x-ray detector system and the x-ray data acquisition system used in the CT industrial imaging system disclosed in the prior invention. The essence of the system is to use a three dimensional cone shaped hard radiation beam which passes through an industrial object such as metal castings and the like with sufficient intensity to develop a light image which can be reconstructed by computer into a three dimensional image of the object. The detector arrangement disclosed has been designed with a number of features to accommodate the attenuated beam's range of energies for a large area field-of-view image. A number of the individual features of the arrangement disclosed are per se known in the art. However, the combination has not heretofore been employed especially with cone beam imaging, object placement and CT three dimensional imaging. At the same time, the detector arrangement disclosed is capable of developing radiographic images.

For a detector of the type described in the preferred embodiment, spatial resolutions of from 0.005" to 0.05" can be achieved. In addition, a low contrast resolution of 0.5% on a 4 millimeter pin is possible. Examples of resolution and voxel size imaged by the detector discussed above are set forth in the following table:

| Volume View ™ Performance Specifications Table* (All scan sequences = 120 sec. & up to 512 slices in Z axis) | | | | | |
|---|---|---|---|---|---|
| Scanning | | Obj. | Voxel | | Dimensional |
| Dia. | Ht. | Dia. | Size | Res. | Accuracy |
| 24.0" | 9.0" | 36.0 | 0.047" cu. | 0.047" 4 lp/cm. | 0.024" |
| 12.0" | 10.0" | 36.0" | 0.023" cu. | 0.023" 8 lp/cm. | 0.012" |
| 8.0" | 8.0" | 12.0" | 0.0156" cu. | 0.0167" 12 lp/cm. | 0.008" |
| 6.0" | 6.0" | 12.0" | 0.012" cu. | 0.013" 15 lp/cm. | 0.006" |
| 3.0" | 3.0" | 12.0" | 0.006" cu. | 0.0065" 30 lp/cm. | 0.003" |

The invention has been described with reference to a preferred embodiment. Obviously, modifications and alterations will occur to others upon reading and understanding the specification. For example, the invention has been described with reference to a CT industrial imaging device. The detector arrangement disclosed can develop radiographic images and, in theory, the detector can be used in medical applications. It is our intention to include all such alterations and modifications insofar as they come within the scope of the present invention.

It is thus the essence of the invention to provide an x-ray detector arrangement per se and system for use therewith, which is capable of developing high resolution images for very large industrial objects.

Having thus defined my invention, I claim:

1. An industrial, non-destructive inspection and imaging system comprising a source of radiation emitting a cone shaped beam of hard radiation at one side of a specimen to be inspected;

a two dimensional scintillation screen on the opposite side of said specimen receiving attenuated radiation beams and generating light photons correlated to the intensity of said radiation beams;

lens means positioned on an axis including a lens at one axial end thereof for collecting said light photons and at least another lens at the opposite axial end of said lens means closely adjacent a glass window plate; said glass plate having a photocathode side and a lens side and said lens means being effective to optically focus substantially all of the collected light photons on the photocathode side of said glass plate;

an intensifier housing having said glass plate at one axial end thereof and aligned with said lens means on said axis, a photocathode at said photocathode side of said glass plate, an intensifier screen parallel to and at a slight axial distance from said photocathode, electrical means between said photocathode and said intensifier screen to generate an electrical potential therebetween whereby photoelectrons in an electron pattern developed at said photocathode are accelerated towards said intensifier screen, said intensifier screen producing an intensified pattern of light photons corresponding to said electron pattern;

a fiberoptic plate on the opposite side of said intensifier screen;

a plurality of fiberoptic conduits arranged in an orderly manner to transmit images from one axial end to the other axial end thereof, said conduits, at one axial end, arranged in side-by-side contact with said fiberoptic plate to substantially encompass an effective area of said fiberoptic plate while each fiberoptic conduit is laterally displaced from one another at the opposite axial end thereof, said plurality of fiberoptic conduits including fiberoptic tapered conduits for reducing the size of two dimensional images transmitted through said fiberoptic conduits; and CCD means connected to each tapered conduit for generating in a bucket brigade manner, electrical analog signals corresponding to the two dimensional image at the end of said fiberoptic conduits, said CCD means being cooled whereby noise from said CCD means is reduced while the image on said intensifier screen is enhanced; and said radiation source being a point source generator for generating a non-pulsed, three dimensional cone beam of transmitted rays of hard radiation;

collimator means associated with said generator for controlling the cone angle and the peripheral configuration of said cone beam;

positioning means for locating said specimen in the path of said cone beam such that a predetermined volumetric portion of said specimen is exposed to said three dimensional cone beam of hard radiation; and said positioning means including means for positioning said specimen in a three dimensional relationship relative to said source and means for intermittently rotating said specimen relative to said point source and said detector means about only one axis of said specimen through predetermined angular increments, said axis being centered at said predetermined volumetric portion of said specimen and not necessarily at said specimen's geometric center.

2. The industrial imaging system of claim 1 further including:
a multi-channel plate adjacent to said photocathode for multiplying the number of electrons generated by said photocathode for each light photon transmitted by said lens means to said photocathode.

3. The industrial imaging system of claim 2 further including said intensifier screen being a phosphor screen and having a vaporized coating of aluminum on its side facing said photocathode for reflecting light photons back towards said fiberoptic plate.

4. The system of claim 1 wherein said CCD means comprise a plurality of CCD chips such that each tapered fiberoptic conduit has a CCD chip in association therewith.

5. The system of claim 4 wherein said intensifier housing encloses said CCD chips as well as said photocathode and said phosphor screen and means for cooling said housing to a temperature no greater than $-20°$ C. whereby not only the dynamics range of said CCD chips is enhanced while the noise is reduced but also the resolution of the image produced at said phosphor screen is increased.

6. The system of claim 5 wherein said scintillation screen has a size of at least 36" by $14\frac{1}{2}$" and substantially all of the two dimensional image projected therefrom is collected by said CCD chips.

7. The system of claim 1 wherein there are at least two CCD devices and further including
a) CCD readout means including shift registers and an amplifier for generating an electrical, analog output signal from each CCD device indicative of the light intensity received in each CCD device at specific locations thereon;
b) multiplexing means for variably controlling i) the time said intensifier is cycled off and on, ii) the timing during which said CCD readout means is activated and iii) the gating of said analog signal; and
c) analog to digital means for converting said analog signal into a series of digital signals, each digital signal corresponding to a pixel.

8. The system of claim 7 wherein said analog to digital means includes means to amplify said analog signal generated by said CCD readout means, means to modify said amplified analog signal as a logarithmic function to account for the attenuation of the beams of hard radiation, means to alter said logarithmic analog signal to filter noise therefrom and an analog to digital device to convert said filtered analog signal to digital signals.

9. The system of claim 7 wherein said CCD readout means is activated by said multiplexer means only when said intensifier is cycled off, each CCD device integrating said light photons while said intensifier is on, and a host computer controlling said multiplexer means for establishing the on time based on a priori information.

10. The system of claim 9 wherein said lens means is fixed in position relative to said intensifier housing, and including
a mirror for reflecting the light emitted from said screen,
focusing means for moving said intensifier in two orthogonal directions relative to said mirror, and
a priori means for analyzing attenuated radiation data during an initial scan of the irradiated object to control said focusing means and said multiplexing means to focus said intensifier while controlling the time period said intensifier is activated.

11. The system of claim 1 further including means for digitizing said analog signal into digitized numbers, means for recording said digitized numbers during the time said rotating means is unactuated and CT means for constructing a three dimensional transparent image of said predetermined volumetric portion from said digitized numbers after a predetermined number of angular rotations whereby a three dimensional image of said specimen can be constructed.

12. The system of claim 1 wherein said scintillation screen extends along orthogonal Y and Z axes;

dynamic flux variation means effective to uniformly vary the intensity of transmitting beams of radiation which strike as attenuated beams of radiation said scintillation screen in said Y and Z directions, said intensity of said beams correlated to the mass density of said specimen along an orthogonal X axis as said specimen rotates about a Y axis such that the intensity of the transmitting beams passing through high mass densities of said specimen at a specific angular rotation is higher than the beam intensity passing through low mass portions of said specimen at a different angular rotation whereby the energy levels of the attenuated beams striking said scintillation device are at lesser variance than that which would occur had the intensity of said transmitting beams been uniform.

13. The system of claim 1 further including dynamic flux integration means for narrowing the variation between the analog signals generated by said CCD means, by varying the time period said CCD means is exposed to the light image from said fiberoptic plate in accordance with the mass density of said specimen at any given angular rotation such that a longer integrating time is provided when the mass density of said specimen penetrated by said radiation over a predetermined volumetric portion is higher than the mass density of said specimen at another predetermined volumetric position, and CT means correlated to said positioning means to adjust the value of said signal recorded by said CCD means.

14. An imaging arrangement for use in a hard radiation system which irradiates a specimen comprising:
 a two dimensional scintillation screen receiving beams of radiation attenuated by a specimen and developing a visible light pattern corresponding to the energy of said beams of attenuated radiation;
 means to focus said light pattern in an intensified manner on a plurality of area charge-coupled devices;
 means to integrate said charge-coupled devices over a fixed time period; and
 means to predetermine said fixed time period in accordance with the mass density of the specimen and control said integrating means accordingly.

15. An industrial, non-destructive inspection and imaging system comprising
 a source of radiation emitting a cone shaped beam of hard radiation at one side of a specimen to be inspected;
 a two dimensional scintillation screen on the opposite side of said specimen receiving attenuated radiation beams and generating light photons correlated to the intensity of said radiation beams;
 lens means positioned on an axis including a lens at one axial end thereof for collecting said light photons and at least another lens at the opposite axial end of said lens means closely adjacent a glass window plate; said glass plate having a photocathode side and a lens side and said lens means being effective to optically focus substantially all of the collected light photons on the photocathode side of said glass plate;
 an intensifier housing having said glass plate at one axial end thereof and aligned with said lens means on said axis, a photocathode at said photocathode side of said glass plate, an intensifier screen parallel to and at a slight axial distance from said photocathode, electrical means between said photocathode and said intensifier screen to generate an electrical potential therebetween whereby photoelectrons in an electron pattern developed at said photocathode are accelerated towards said intensifier screen, said intensifier screen producing an intensified pattern of light photons corresponding to said electron pattern;
 a fiberoptic plate on the opposite side of said intensifier screen;
 a plurality of fiberoptic conduits arranged in an orderly manner to transmit images form one axial end to the other axial end thereof, said conduits, at one axial end, arranged in side-by-side contact with said fiberoptic plate to substantially encompass an effective area of said fiberoptic plate while each fiberoptic conduit is laterally displaced from one another at the opposite axial end thereof, said plurality of fiberoptic conduits including fiberoptic tapered conduits for reducing the size of two dimensional images transmitted through said fiberoptic conduits; and
 CCD means connected to each tapered conduit for generating in a bucket brigade manner, electrical analog signals corresponding to the two dimensional image at the end of said fiberoptic conduits, said CCD means being cooled whereby noise from said CCD means is reduced while the image on said intensifier screen is enhanced; and
 wherein said lens means is affixed to said intensifier housing and drive means are provided for moving said intensifier along said axis whereby said image from said scintillation screen is focused on said photocathode.

16. The industrial imaging system of claim 15 wherein said lens means includes at least one zoom lens having at least one magnifying lens movable over said first lens to permit close-up views of a portion of said image produced from said scintillation screen without having to refocus said lens means.

17. The system of claim 16 wherein said plurality of fiberoptic conduits include straight conduits which are in the form of parallelpipeds with side wall surfaces forming an acute angle with said fiberoptic plate.

* * * * *